United States Patent [19]

Reid

[11] 4,051,086
[45] Sept. 27, 1977

[54] ABSORPTION RATE OF ABSORBENT POLYMERS BY TREATING WITH GLYOXAL

[75] Inventor: Albert Richard Reid, Hockessin, Del.

[73] Assignee: Hercules Incorporated, Wilmington, Del.

[21] Appl. No.: 670,484

[22] Filed: Mar. 25, 1976

[51] Int. Cl.$^2$ .............................................. C08L 1/02
[52] U.S. Cl. ..................... 260/17.4 GC; 47/DIG. 10; 128/284; 128/296; 260/17.4 R; 260/17.4 CL; 260/17 A; 260/73 R; 260/17.4 ST; 526/55; 528/493
[58] Field of Search ................... 260/17.4 R, 17.4 CL, 260/17.4 ST, 17.4 GC, 17 A, 73 R; 528/493; 526/55

[56] References Cited
PUBLICATIONS

Chem. Absts., 77 (1972) 49639u, "Dialdehyde-Crosslinked Acrylamide Polymers for Soil Stabilization", Bracke.

*Primary Examiner*—Edward M. Woodberry
*Attorney, Agent, or Firm*—William S. Alexander

[57] ABSTRACT

Water-absorbent crosslinked polymers are improved in their wicking capacity by treatment of their surface with glyoxal. The polymer can be a polysaccharide—acrylamide graft copolymer or a polymer or copolymer of acrylamide and/or sodium acrylate or sodium methacrylate.

11 Claims, No Drawings

ABSORPTION RATE OF ABSORBENT POLYMERS BY TREATING WITH GLYOXAL

This invention relates to the preparation of water-insoluble, highly absorbent synthetic polymers. Specifically, it relates to the preparation of such products based on polymers and copolymers of acrylamide.

My copending U.S. patent application Ser. No. 625,332, filed Oct. 23, 1975, teaches the preparation of highly absorbent materials based on polysaccharide—polyacrylamide graft copolymers. As taught in that application, acrylamide, or preferably a mixture of acrylamide and a copolymerizable vinyl monomer such as sodium acrylate, is polymerized in the pressure of cellulose under the influence of a free radical catalyst system and in the presence of a divinyl crosslinker for the resultant polymer so that polymerization and crosslinking take place simultaneously. The product that results is principally a crosslinked graft copolymer of cellulose and the acrylamide copolymer. It is believed that there is also a portion of free (i.e., non-grafted) acrylamide polymer which is tightly bound via divinyl crosslinking to the graft copolymer or to the polysaccharide backbone and is not separable therefrom. Accordingly, the product is referred to simply as a graft copolymer. The simultaneous grafting and crosslinking result in an almost totally insoluble mixture having a high absorbent capacity for water and saline solutions.

In evaluating the absorbent qualities of the grafted polysaccharides, two characteristics are regarded as important. One is the total absorbent capacity of the material and the other is the rate at which the absorption takes place, i.e., the wicking ability of the material.

As is shown in my referenced copending patent application, the crosslinked, grafted copolymer has quite good absorbency at a relatively low level of divinyl crosslinking. At lower crosslinkage levels, however, the wicking ability of the product is not optimum when the product is in powder or particulate form. In order to achieve better wicking with these powdered products, it is necessary to increase the amount of divinyl crosslinker up to about 10% of the total graft copolymer. It is theorized that the materials of lower wicking ability gel rapidly at the point of initial contact of the aqueous solution with the surface of the polymer particle, thus reducing the rate at which the liquid can pass through the surface and into the interior of the absorbent mass.

I have found that by treatment of the surface of a powdered crosslinked, grafted polysaccharide with about 0.2 to 5% by weight of glyoxal, its wicking action can be significantly increased without increasing the amount of divinyl crosslinker above about 2%.

It is known (U.S. Pat. Nos. 2,879,268 and 3,072,635) to treat water-soluble polysaccharides with glyoxal. This is done to facilitate the dissolution of these materials in water. This improvement is believed to come about because the glyoxal decreases the water sensitivity of the surface of the treated polysaccharide, thus diminishing the tendency of the surface toward gelling. While this is a similar mechanism to that proposed for the present invention, it is nonetheless surprising to find that the method is effective for the materials contemplated by this invention since, as will be demonstrated hereinafter, the glyoxal treatment does not appear to be effective in improving the wicking of other crosslinked absorbent cellulose derivatives.

The crosslinked polyacrylamide—polysaccharide graft copolymer to which this invention is applicable is the product of simultaneously reacting acrylamide or methacrylamide and at least one other water-soluble vinyl monomer and a water-soluble divinyl monomer with the aid of a free radical catalyst system in the presence of a polysaccharide host material. The preferred second monomers are acrylic acid or methacrylic acid and their alkali metal salts. Examples of still other monomers which can be used as the comonomer with acrylamide or methacrylamide are the alkali metal salts of 2-acrylamido-2-methyl propane sulfonic acid, alkali metal salts of sulfopropylacrylic acid, 1,2-dimethyl-5-vinylpyridinium methyl sulfate, and 2-methacryloyloxyethyl trimethyl ammonium methyl sulfate.

The polyacrylamide—polysaccharide graft copolymer is crosslinked with a divinyl compound which polymerizes via the same free radical mechanism as is employed to polymerize the vinyl monomers mentioned above. The preferred crosslinker is methylene-bis-acrylamide (MBA). Other divinyl monomers which can be used for crosslinking are methylene-bis-methacrylamide and quaternary compounds such as, e.g., quaternized 2,5-divinyl pyridine.

Various polysaccharide furnishes can be employed to prepare graft copolymers in particulate form to which the process of this invention is applicable. These include fibrous chemical cotton, fine-cut cotton, and wood pulps, activated polysaccharides such as oxidized cellulose and pre-irradiated celluloses and starches; hydrolyzed polysaccharides such as hydrocelluloses; various types of starch such as corn, potato, wheat starches, as is, or pregelatinized; guar gum, and various water-insoluble derivatives of cellulose, starch, and other polysaccharides such as carboxymethyl cellulose of D.S. 0.05 to 0.25 and hydroxyethyl cellulose of M.S. 0.05 to 0.25, and crosslinked hydroxyethyl cellulose of M.S. 0.3 to 3. Oxidized cellulose and regular cotton and wood pulps were preferred.

The preferred products for application of the invention contain from about 10 to 60% by weight of the host polysaccharide and about 40 to 90% by weight of crosslinked acrylamide polymer. The acrylamide component will usually make up about 10 to 50% of the synthetic polymer portion. Preferably, the host polysaccharide will be about 40 to 50% of the composition with the synthetic polymer being about 50 to 60%. Preferably, the synthetic polymer portion will contain about 20 to 30% of the acrylamide component. Further, the preferred products contain about 0.2 to 2%, and preferably about 0.5 to 2%, based on the combined weight of monomers, of the divinyl crosslinking compound.

The method of the invention is also applicable to crosslinked acrylamide and sodium acrylate polymer powders which are not grafted to polysaccharide backbones. These latter are known commerical products which can be homopolymers of acrylamide, or homopolymers of ammonium or alkali metal salts of acrylic acid or methacrylic acid or, more preferably, copolymers of acrylamide or methacrylamide with acrylic or methacrylic acid salts in substantially any proportions. Also applicable are the products prepared by acid or basic hydrolysis of crosslinked acrylamide or methacrylamide homopolymers to convert a portion of the amide groups to the acid form or to the acid salt form. Yet another applicable polymer is acrylonitrile or methacrylonitrile homopolymer hydrolyzed to give amide and acid groups.

To apply the glyoxal to the crosslinked polymer, the particulate polymer is first slurried in a nonsolvent such as, e.g., acetone A dilute aqueous solution of glyoxal is added slowly to the slurry with stirring. The pH of the slurry is adjusted to about 5.5 to 6.0 and the stirring is continued for a time sufficient to allow the required amount of glyoxal to react with the surface of the particle. The amount of glyoxal required is about 0.2 to 5% by weight based on the weight of polymer and preferably about 0.2 to 2%. The polymer is then removed from the slurry medium, washed with a nonsolvent and dried at an elevated temperature. The heat applied for drying appears to assist in developing absorbency. A temperature of about 50° to 75° C. is preferred.

The absorbent products resulting from the practice of the invention can be used in a variety of applications where absorbency is a desideratum. In particular, they are useful in applications such as feminine hygiene products, dental sponges, surgical sponges, and disposable diapers. Other applications are as moisture barriers, e.g., for underground cables and foundations of buildings, for erosion control, and as soil conditions.

Without wishing to be bound to or limited by any particular theory regarding the mechanism by which the absorbency is improved by following the method of this invention, it appears possible that a low level of surface crosslinking between glyoxal and polymer may be the reason.

The absorbent products can be used alone or in any of the above applications. However, for economic reasons, they can be blended with conventional absorbent cellulosics such as crosslinked carboxymethyl cellulose, chemical cotton, wood pulp or cotton staple. Relatively small amounts of the invention product can effect relatively large increases in absorbency over that of the cellulosic absorbents alone.

The products are tested for absorbent capacity and wicking action by means of the so-called "CAP" (capillary or wicking action) test. The apparatus employed for the CAP test consists of a Buchner fritted glass funnel, with a rubber tube attached to its neck; the tube is attached at the other end to a 50 ml. burette. The burette is filled with the test solution, and the level of liquid is allowed to rise until it just makes contact with the bottom of the frit in the funnel. The level of liquid in the burette can be anywhere from 0 to 60 cm. below the bottom of this frit. A one-gram test sample is placed on top of the frit and a weight exerting a pressure of from 0.1 to 0.4 p.s.i. is applied over the entire surface of the sample. The test is then begun, and the loss of fluid in the burette is monitored as a function of time to give the rate of absorption. When equilibrium is reached, the capacity is calculated by dividing the total fluid absorbed at equilibrium, or at the end of 45 minutes, by the weight of the polymer sample. The conditions used with the CAP test for this work are:

1. Pressure exerted on the sample was 0.11 p.s.i.
2. All of the tests were done with the liquid in the burette 2 cm. below the fritted glass initially. This level was allowed to change continuously as absorption occurred.

EXAMPLE 1

Crosslinked oxidized cellulose-polyacrylamide graft copolymer (51% polyacrylamide, 0.5% MBA crosslinker by weight) in fine particle form was slurried in acetone and an aqueous solution of glyoxal sufficient to contain 0.5% glyoxal based on weight of the graft copolymer was added dropwise to the stirred slurry. The pH of the slurry was adjusted to between about 5.5 and 5.6 and stirring was continued for one hour at room temperature. Excess liquid was removed and the product was washed several times with acetone and dried at 60° C. under reduced pressure.

The product and an untreated control (Control A) were tested for absorption rate of 1% NaCl solution via the CAP test described hereinabove. In a 45-minute test, the glyoxal-treated material was several times superior to the untreated material. Results are recorded in Table 1.

EXAMPLE 2

The crosslinked grafted cellulose employed in Example 1 was treated with 2% glyoxal via the same procedure and tested in the same manner. Again the results were significantly improved over the untreated control. Results are recorded in Table 1.

EXAMPLE 3

A second crosslinked grafted cellulose prepared with unoxidized cellulose (50% polyacrylamide, 0.5% MBA crosslinker) was treated with 0.5 % glyoxal as described in Example 1. This material and an untreated control were subjected to the CAP test. The glyoxal-treated material was significantly better in rate of absorption and absorption capacity. Results are recorded in Table 1. Both the control and the glyoxal-treated material formed gels when slurried in water at 1% and even at 0.5% concentration, indicating no change in the total water absorption capacity of greater than 200 ml./g. of absorbent.

EXAMPLE 4

The following crosslinked grafted polysaccharides were treated with 2% glyoxal:
  4a. Gelatinized wheat starch containing 52% polyacrylamide graft which contained 0.5% MBA;
  4b. Corn starch containing 53% polyacrylamide graft which contained 0.5% MBA;
  4c. Guar gum containing 51% polyacrylamide graft which contained 0.5% MBA.

Each of these was tested via the CAP test along with its appropriate untreated control. In each case the glyoxaltreated material exhibited substantially better wicking action and absorption capacity. Results are recorded in Table 1.

TABLE 1

| CAP TEST DATA FOR GLYOXAL-TREATED CROSSLINKED GRAFTED POLYSACCHARIDES | | | | | | | | | | | | |
|---|---|---|---|---|---|---|---|---|---|---|---|---|
| | | Volume of 1% NaCl Solution Absorbed (ml./g.) at Various Times (Minutes) in Water | | | | | | | | | | |
| Example | Type of Sample[a] | 1 | 3 | 5 | 10 | 15 | 20 | 25 | 30 | 35 | 40 | 45 |
| Control 1 | Grafted cellulose | 0.5 | 0.7 | 0.8 | 1.0 | 1.2 | 1.4 | 1.5 | 1.6 | 1.6 | 1.7 | — |
| 1 | Glyoxal-treated grafted cellulose (0.5% glyoxal) | 1.2 | 2.4 | 2.9 | 3.8 | 4.4 | 4.8 | 5.1 | 5.3 | 5.6 | 5.8 | 6.0 |
| 2 | Glyoxal-treated grafted cellulose | 1.8 | 3.5 | 4.5 | 5.8 | 6.5 | 7.0 | 7.4 | 7.7 | 7.9 | 8.1 | 8.2 |

TABLE 1-continued
CAP TEST DATA FOR GLYOXAL-TREATED CROSSLINKED GRAFTED POLYSACCHARIDES

| Example | Type of Sample[a] | Volume of 1% NaCl Solution Absorbed (ml./g.) at Various Times (Minutes) in Water | | | | | | | | | | |
|---|---|---|---|---|---|---|---|---|---|---|---|---|
| | | 1 | 3 | 5 | 10 | 15 | 20 | 25 | 30 | 35 | 40 | 45 |
| Control 3 | Grafted cellulose | 0.6 | 1.3 | 1.9 | 2.7 | 3.1 | 3.4 | 3.8 | 4.3 | 4.5 | 4.7 | 4.9 |
| 3 | Glyoxal-treated grafted cellulose (2% glyoxal) | 1.2 | 3.0 | 4.4 | 6.6 | 8.1 | 9.0 | 9.5 | 9.9 | 10.1 | 10.2 | 10.2 |
| Control 4a | Grafted gelatinized wheat starch | 0.4 | 0.7 | 0.8 | 1.1 | 1.4 | 1.7 | 1.9 | 2.1 | 2.5 | 2.4 | 2.5 |
| 4a | Glyoxal-treated gelatinized wheat starch (2% glyoxal) | 1.3 | 3.0 | 4.6 | 7.5 | 8.9 | 9.6 | 10.0 | 10.2 | 10.4 | 10.5 | 10.6 |
| Control 4b | Grafted corn starch | 0.3 | 0.5 | 0.7 | 0.9 | 1.2 | 1.4 | 1.6 | 1.7 | 1.8 | 1.9 | 2.1 |
| 4b | Glyoxal-treated corn starch (2% glyoxal) | 0.9 | 1.9 | 2.8 | 4.2 | 5.1 | 5.7 | 6.2 | 6.7 | 7.0 | 7.2 | 7.5 |
| Control 4c | Grafted guar gum | 0.3 | 0.4 | 0.5 | 0.8 | 1.2 | 1.5 | 1.9 | 2.3 | 2.5 | 3.1 | 3.3 |
| 4c | Glyoxal-treated guar gum (2% glyoxal) | 1.2 | 2.4 | 3.6 | 5.0 | 6.0 | 6.7 | 7.2 | 7.7 | 8.1 | 8.4 | 8.7 |

[a]Glyoxal concentration is based on the weight of crosslinked, grafted polysaccharide.

EXAMPLE 5

Granular particles of a copolymer of about 70% acrylamide units and 30% sodium acrylate units and crosslinked with about 0.5% MBA were treated with 2% glyoxal as described in Example 1. CAP test data for this material and its untreated control are recorded in ple 1 and tested for absorbency rate via the CAP test. Results are recorded in a Table 2.

In each case, Examples 5 through 8, the product produced according to the invention is significantly better with respect to absorption capacity and rate of absorption than its untreated control when evaluated via the CAP test.

TABLE 2
CAP TEST DATA FOR GLYOXAL-TREATED CROSSLINKED ACRYLAMIDE COPOLYMERS

| Example | Type of Sample[a] | Volume of 1% NaCl Solution Absorbed (ml./g.) at Various Times in Minutes | | | | | | | | | | |
|---|---|---|---|---|---|---|---|---|---|---|---|---|
| | | 1 | 3 | 5 | 10 | 15 | 20 | 25 | 30 | 35 | 40 | 45 |
| Control 5 | Crosslinked acrylamide-sodium acrylate copolymer (0.5% MBA) | 0.3 | 0.5 | 0.7 | 1.1 | 1.4 | 1.5 | 1.9 | 2.0 | 2.1 | 2.2 | 2.4 |
| 5 | 2% Glyoxal-treated crosslinked acrylamide-sodium acrylate copolymer (0.5% MBA) | 1.5 | 3.5 | 4.7 | 6.8 | 8.0 | 8.8 | 9.6 | 10.1 | 10.7 | 11.0 | 11.4 |
| Control 6 | Crosslinked acrylamide-sodium acrylate copolymer (0.25% MBA) | 0.5 | 0.6 | 0.7 | 0.9 | 1.1 | 1.2 | 1.3 | 1.4 | 1.5 | 1.6 | 1.7 |
| 6 | 2% Glyoxal-treated crosslinked acrylamide-sodium acrylate copolymer (0.25% MBA) | 1.7 | 3.5 | 5.1 | 6.9 | 8.4 | 9.1 | 9.5 | 9.7 | 9.9 | 10.1 | 10.4 |
| Control 7 | Crosslinked acrylamide-sodium acrylate copolymer (0.5% MBA) | 0.4 | 0.6 | 0.7 | 1.0 | 1.2 | 1.3 | 1.4 | 1.6 | 1.6 | 1.7 | 1.7 |
| 7 | 0.5% Glyoxal-treated crosslinked acrylamide-sodium acrylate copolymer (0.5% MBA) | 1.1 | 2.7 | 4.2 | 6.3 | 7.7 | 8.7 | 9.3 | 9.8 | 10.2 | 10.5 | 10.8 |
| Control 8 | Crosslinked poly-(sodium acrylate) (0.5% MBA) | 0.2 | 0.3 | 0.5 | 0.6 | 0.7 | 0.8 | 1.0 | 1.1 | 1.2 | 1.4 | 1.5 |
| 8 | 2% Glyoxal-treated poly(sodium acrylate) (0.5% MBA) | 0.8 | 2.0 | 2.9 | 4.8 | 6.1 | 6.9 | 7.6 | 8.0 | 8.3 | 8.5 | 8.8 |

[a]Glyoxal concentration is based on the weight of the crosslinked polymer.

EXAMPLE 6

Example 5 was repeated with a copolymer of 30% acrylamide units and 70% sodium acrylate units crosslinked with 0.25% MBA. CAP test data are recorded in Table 2.

EXAMPLE 7

Example 5 was repeated with a copolymer of 30% acrylamide units and 70% sodium acrylate units crosslinked with 0.5% MBA. This material was treated with 0.5% glyoxal. CAP test data are recorded in Table 2.

EXAMPLE 8

Poly(sodium acrylate) crosslinked with 0.5% MBA and treated with 2% glyoxal was prepared as in Exam-

EXAMPLE 9

To demonstrate the ineffectiveness of the invention with respect to other known crosslinked highly absorbent cellulose derivatives, a series of crosslinked carboxymethyl cellulose (CMC) were tested with and without glyoxal treatment. Glyoxal treatment was effected as taught hereinabove. Results are shown in Table 3.

As is very effectively demonstrated in Table 3, only the epichlorohydrin crosslinked CMC was improved even slightly by the glyoxal treatment. In that case the improvement was so slight that it would not be commercially attractive. In other cases, no improvement or even a deterioration of wicking was observed.

TABLE 3

CAP TEST FOR GLYOXAL-TREATED CROSSLINKED CMC's

| | | Volume of 1% NaCl Solution Absorbed (ml./g.) at Various Times in Minutes | | | | | | | | | | |
|---|---|---|---|---|---|---|---|---|---|---|---|---|
| Example | Type of Sample[a] | 1 | 3 | 5 | 10 | 15 | 20 | 25 | 30 | 35 | 40 | 45 |
| 8a | Epichlorohydrin crosslinked CMC (densified) | 1.9 | 4.0 | 5.6 | 8.6 | 10.3 | 11.3 | 11.7 | 12.2 | 12.5 | 12.5 | 12.5 |
| 8b | Glyoxal-treated 8a (2% glyoxal) | 2.6 | 6.1 | 8.6 | 11.4 | 12.4 | 13.0 | 13.4 | 13.7 | 14.0 | 14.1 | 14.3 |
| 8c | Acid crosslinked CMC from fine-cut chemical cotton; not densified | 2.3 | 5.5 | 7.7 | 10.5 | 11.0 | 11.1 | 11.1 | 11.1 | — | — | — |
| 8d | Glyoxal-treated 8c (2% glyoxal) | 4.1 | 6.8 | 7.2 | 8.2 | 8.7 | 9.0 | 9.2 | 9.3 | 9.4 | 9.5 | 9.6 |
| 8e | Glyoxal-treated 8c (0.5% glyoxal) | 4.7 | 7.4 | 8.0 | 8.8 | 9.2 | 9.4 | 9.5 | 9.6 | 9.7 | 9.7 | 9.7 |
| 8f | Acid crosslinked CMC from chemical cotton | 1.2 | 3.3 | 5.0 | 8.7 | 9.4 | 9.4 | 9.6 | 9.7 | 9.7 | 9.7 | — |
| 8g | Glyoxal-treated 8f (2% glyoxal) | 1.6 | 4.2 | 5.0 | 5.7 | 6.1 | 6.3 | 6.3 | 6.3 | — | — | — |
| | | 1.1 | 3.0 | 4.4 | 5.6 | 6.0 | 6.1 | 6.2 | 6.2 | 6.2 | 6.2 | — |
| 8h | Fitz-milled acid crosslinked CMC from chemical cotton | 2.4 | 6.3 | 8.9 | 10.0 | 10.1 | 10.2 | 10.2 | 10.2 | 10.2 | — | — |
| 8i | Glyoxal-treated 8b | 3.1 | 5.5 | 6.0 | 6.9 | 8.0 | 8.1 | 8.5 | 8.8 | 9.0 | 9.3 | 9.5 |

[a]The glyoxal concentration is based on the weight of crosslinked CMC.

What I claim and desire to protect by Letters Patent is:

1. A method of increasing the water or saline solution absorption rate of a water-insoluble, crosslinked polymer selected from the class consisting of acrylamide homopolymer, copolymers of acrylamide and a second vinyl monomer copolymerizable therewith, homopolymers of sodium acrylate, homopolymers of sodium methacrylate, and polysaccharides grafted with copolymers of acrylamide and a second vinyl monomer copolymerizable therewith, which method comprises applying to the surface of particles of said polymer about 0.2 to 5% by weight of glyoxal.

2. A method according to claim 1 wherein the water-insoluble crosslinked polymer is cellulose having grafted thereto a copolymer of about 10 to 50% acrylamide and 50 to 90% sodium acrylate crosslinked with bis-methylene-bis-acrylamide.

3. A method according to claim 1 wherein the water-insoluble crosslinked polymer is a copolymer of acrylamide and sodium acrylate crosslinked with methylene-bis-acrylamide.

4. A method of increasing the water or saline solution absorption rate of a water-insoluble, crosslinked polymer selected from the class consisting of acrylamide hompolymer, copolymers of acrylamide and a second vinyl monomer copolymerizable therewith, homopolymers of sodium acrylate, homopolymers of sodium methacrylate, and polysaccharides grafted with copolymers of acrylamide and a second vinyl monomer copolymerizable therewith, which method comprises forming a slurry of particles of the crosslinked polymer in a nonsolvent liquid, adding to said slurry glyoxal in an amount equal to about 0.2 to 2% by weight of the polymer, adjusting the pH of the slurry to about 5.5 to 5.6, removing the polymer from the slurry and drying at about 50 to 75° C. to remove residual slurrying liquid.

5. A method according to claim 4 wherein the water-insoluble crosslinked polymer is cellulose having grafted thereto a copolymer of about 10 to 50% acrylamide and 50 to 90% sodium acrylate crosslinked with bis-methylene-bis-acrylamide.

6. A method according to claim 4 wherein the water-insoluble crosslinked polymer is a copolymer of acrylamide and sodium acrylate crosslinked with methylene-bis-acrylamide.

7. A method according to claim 4 wherein the water-insoluble crosslinked polymer is guar gum having grafted thereto a copolymer of about 10 to 50% acrylamide and 50 to 90% sodium acrylate crosslinked with methylene-bis-acrylamide.

8. A method according to claim 4 wherein the water-insoluble crosslinked polymer is starch having grafted thereto a copolymer of about 10 to 50% acrylamide and 50 to 90% sodium acrylate crosslinked with methylene-bis-acrylamide.

9. An acrylic polymer selected from the class consisting of
   a. homopolymers of water-soluble acrylic acid salts,
   b. homopolymers of water-soluble methacrylic acid salts,
   c. homopolymers of acrylamide,
   d. copolymers of acrylamide and one of the salts specified in (a) and (b) in any proportion, and
   e. graft copolymers of a water-insoluble, water wettable polysaccharide, acrylamide and a second vinyl polymer copolymerizable therewith, said acrylic polymer being crosslinked via a divinyl monomer and being in particulate form and having its particle surfaces treated with about 0.2 to 5% by weight of glyoxal.

10. A graft copolymer of cellulose, acrylamide and an acrylic acid salt crosslinked via methylene bis-acrylamide and comprising about 10 to 90% by weight of cellulose, said copolymer being in particulate form and having its particle surfaces treated with about 0.2 to 2% by weight of glyoxal.

11. A copolymer of acrylamide and a water-soluble acrylic acid salt in any proportion, said copolymer being crosslinked via methylene bis-acrylamide, being in particulate form and having its particle surfaces treated with about 0.2 to 2% by weight of glyoxal.

* * * * *